United States Patent
Kaarigstad et al.

(10) Patent No.: US 9,587,490 B2
(45) Date of Patent: Mar. 7, 2017

(54) TEST EQUIPMENT SIMULATING MULTIPLE FLUID SEQUENCES

(71) Applicant: SCHLUMBERGER NORGE AS, Stavanger (NO)

(72) Inventors: Håvard Kaarigstad, Sola (NO); Christine Mo, Sandsli (NO)

(73) Assignee: SCHLUMBERGER NORGE AS, Stavanger (NO)

( * ) Notice: Subject to any disclaimer, the term of this patent is extended or adjusted under 35 U.S.C. 154(b) by 0 days.

(21) Appl. No.: 14/360,393

(22) PCT Filed: Nov. 23, 2012

(86) PCT No.: PCT/EP2012/073462
§ 371 (c)(1),
(2) Date: May 23, 2014

(87) PCT Pub. No.: WO2013/076242
PCT Pub. Date: May 30, 2013

(65) Prior Publication Data
US 2014/0319080 A1    Oct. 30, 2014

Related U.S. Application Data

(60) Provisional application No. 61/568,952, filed on Dec. 9, 2011, provisional application No. 61/563,262, filed on Nov. 23, 2011.

(51) Int. Cl.
*G01N 33/28*    (2006.01)
*E21B 49/10*    (2006.01)
(Continued)

(52) U.S. Cl.
CPC .............. *E21B 49/10* (2013.01); *E21B 49/00* (2013.01); *G01N 33/2823* (2013.01); *G01N 7/10* (2013.01)

(58) Field of Classification Search
CPC ...... G01N 33/2823; E21B 49/00; E21B 49/10
(Continued)

(56) References Cited

U.S. PATENT DOCUMENTS 2,296,852 A * 9/1942 Horner .................. E21B 49/005
                                                              436/31
2,662,395 A * 12/1953 Brazier ................. E21B 25/005
                                                              175/249
(Continued)

FOREIGN PATENT DOCUMENTS

WO    2008144165 A1    11/2008

OTHER PUBLICATIONS

McGowen, J. M. et al, SPE paper 18212, 1988, 13 pages.*
(Continued)

*Primary Examiner* — Arlen Soderquist (57) ABSTRACT

A well fluid test device includes a cell body having a first end port disposed on an upper end of the cell body, a second end port disposed on a lower end of the cell body, a first lateral port disposed on a side of the cell body, and a second lateral port disposed on a side of the cell body, and a filter medium disposed in the cell body, wherein the first and second lateral ports are disposed above the filter medium. A method of evaluating a fluid includes injecting a fluid into a well fluid test device, the well fluid test device having a filter medium, heating the fluid in the well fluid test device, establishing a pressure differential across the filter medium, establishing a filter cake on the filter medium, and maintaining at least one of a temperature and a pressure in the well fluid test device.

19 Claims, 6 Drawing Sheets

(51) Int. Cl.
*E21B 49/00* (2006.01)
*G01N 7/10* (2006.01)

(58) Field of Classification Search
USPC .......... 73/149, 434, 152.11, 152.05–152.07; 166/250.17; 436/25, 29–31
See application file for complete search history.

(56) References Cited

U.S. PATENT DOCUMENTS

| | | | | |
|---|---|---|---|---|
| 2,705,418 A * | 4/1955 | Francis | ............. | G01N 15/0826 73/38 |
| 2,982,704 A * | 5/1961 | Shelton | ............. | G01N 1/04 205/159 |
| 3,286,510 A * | 11/1966 | Parker | ............. | G01N 33/00 210/321.87 |
| 3,934,455 A * | 1/1976 | Harrisberger | ............. | G01N 33/24 436/25 |
| 4,233,840 A * | 11/1980 | Goss | ............. | G01N 33/24 73/152.08 |
| 4,555,934 A * | 12/1985 | Freeman | ............. | G01N 15/0826 73/38 |
| 4,573,342 A * | 3/1986 | Jones | ............. | G01N 15/08 73/38 |
| 4,599,891 A * | 7/1986 | Brauer | ............. | G01N 15/0806 73/38 |
| 4,753,107 A * | 6/1988 | Reed | ............. | G01N 15/0806 73/38 |
| 4,799,382 A * | 1/1989 | Sprunt | ............. | G01N 15/088 378/4 |
| 4,996,872 A * | 3/1991 | Mueller | ............. | G01N 15/0806 73/38 |
| 5,050,493 A * | 9/1991 | Prizio | ............. | B30B 9/06 100/106 |
| 5,167,139 A * | 12/1992 | Lafargue | ............. | G01N 33/241 73/38 |
| 5,174,966 A * | 12/1992 | Durand | ............. | G01N 33/241 196/14.52 |
| 5,263,360 A * | 11/1993 | Blauch | ............. | C09K 8/58 166/250.02 |
| 5,269,999 A * | 12/1993 | Smesny | ............. | B29C 43/18 264/112 |
| 5,297,420 A * | 3/1994 | Gilliland | ............. | G01N 15/08 73/38 |
| 5,520,822 A * | 5/1996 | Sun | ............. | B01D 29/01 204/572 |
| 5,637,796 A * | 6/1997 | Deruyter | ............. | G01N 15/0806 73/152.09 |
| 5,878,374 A * | 3/1999 | Buchanan | ............. | B01D 37/02 210/143 |
| 6,055,874 A * | 5/2000 | Onan | ............. | E21B 49/00 73/865.6 |
| 6,110,875 A * | 8/2000 | Tjon-Joe-Pin | ............. | C04B 24/38 166/246 |
| 6,543,276 B2 | 4/2003 | Murphy et al. | | |
| 6,910,535 B2 * | 6/2005 | Tare | ............. | C09K 8/50 166/250.14 |
| 7,472,588 B2 * | 1/2009 | Slavin | ............. | G01N 15/08 324/376 |
| 7,549,320 B2 * | 6/2009 | Funkhouser | ............. | G01N 3/10 73/37 |
| 7,552,648 B2 * | 6/2009 | McMechan | ............. | G01N 3/12 73/803 |
| 7,900,504 B2 * | 3/2011 | Huynh | ............. | G01N 15/08 73/38 |
| 8,312,920 B2 * | 11/2012 | Tehrani | ............. | G01N 1/34 166/267 |
| 9,128,021 B2 * | 9/2015 | Oh | ............. | G01N 15/0806 |
| 2008/0236891 A1 * | 10/2008 | Huynh | ............. | G01N 15/08 175/48 |
| 2009/0029878 A1 * | 1/2009 | Bicerano | ............. | C09K 8/035 507/107 |
| 2009/0217776 A1 | 9/2009 | Jamison | | |
| 2009/0286701 A1 * | 11/2009 | Davidson | ............. | C09K 8/52 507/235 |
| 2010/0133204 A1 * | 6/2010 | Tehrani | ............. | G01N 33/2823 210/785 |
| 2010/0139914 A1 * | 6/2010 | Tehrani | ............. | G01N 33/241 166/250.17 |

OTHER PUBLICATIONS

Harris, P. C. et al, SPE Production Engineering 1989, 189-193.*
Navarrete, R. C. et al, SPE paper 28529, 1994, 15 pages.*
Armstrong , K. et al, Oilfield Review 1995, 34-51.*
Burnett, D. B. et al, SPE paper 37125, 1996, 12 pages.*
Ladva, H. K. J. et al, SPE paper 39439, 1998, 12 pages.*
Bazin, B. et al, SPE Journal 1999, 4, 360-367.*
Cantu, L. A. et al, SPE Production Engineering 1990, 253-260.*
Beall, B. B. et al, SPE 36429, 1996, 13 pages.*
Longeron, D. G. et al, SPE 48988, 1998, 15 pages.*
Longeron, D. G. et al, SPE 58737, 2000, 13 pages.*
Navarrete, R. C. et al, IADC/SPE 62732, 2000, 20 pages.*
Todd, B. et al, SPE 68968, 2001, 9 pages.*
Constien, V. G., SPE 112497, 2008, 10 pages.*
International Search Report and Written Opinion of PCT Application Serial No. PCT/EP2012/073462 dated Jun. 5, 2013 (8 pages).
Marquez, et al., "Laboratory Evaluation of RDG Breakers Under Linear and Radial Flow Conditions", SPE 127769, presented at 2010 SPE International Symposium and Exhibition on Formation Damage Control held in Lafayette, Louisiana, USA, Feb. 10-12, 2010, 13 pages.

* cited by examiner

TEST EQUIPMENT SIMULATING MULTIPLE FLUID SEQUENCES

BACKGROUND ART

When drilling or completing wells in earth formations, various fluids typically are used in the well for a variety of reasons. The fluid may be either water-based or oil-based. For the purposes herein, such fluid will be referred to as "well fluid." Common uses for well fluids include: lubrication and cooling of drill bit cutting surfaces while drilling generally or drilling-in (i.e., drilling in a targeted petroliferous formation), transportation of "cuttings" (pieces of formation dislodged by the cutting action of the teeth on a drill bit) to the surface, controlling formation fluid pressure to prevent blowouts, maintaining well stability, suspending solids in the well, minimizing fluid loss into and stabilizing the formation through which the well is being drilled, minimizing fluid loss into the formation after the well has been drilled and during completion operations such as, for example, perforating the well, replacing a tool, attaching a screen to the end of the production tubulars, gravel-packing the well, or fracturing the formation in the vicinity of the well, displacing the fluid within the well with another fluid, cleaning the well, testing the well, fluid used for implacing a packer, abandoning the well or preparing the well for abandonment, and otherwise treating the well or the formation.

A variety of compounds may be added to well fluids to enhance performance. Among these compounds are fluid loss control agents, which act by coating the walls of the wellbore as the well is drilled, with a thin layer of low-permeability filter cake. The filter cake helps to reduce the amount of base fluid lost to the formation and prevents undesirable variations in the density and rheology of the drilling fluid. Additionally, the filter cake helps prevent formation damage in the reservoir, which may be caused by blockage of formation pores through invasion of wellbore fluid. Filter cake also provides a barrier to prevent the influx and efflux of drilling fluids between the wellbore and the formation. Suitable fluid loss control additives, for both water-based and oil-based drilling fluids include modified starches, synthetic resins, modified lignites, asphaltic compounds, gilsonites, and a wide range of other polymeric and non-toxic fluid loss control materials. Such fluid loss control agents may be generally used in drilling fluids, or may be used in gel pills used to prevent fluid loss in a particular zone of the wellbore.

The role of the fluid loss characteristics of the well fluid demands that the properties of the well fluid are carefully monitored throughout the operation, and that corrective measures are taken in time to maintain required specifications of the fluids in the operation. Standard equipment for evaluating fluid efficiency, e.g. filter cake breaker fluid efficiency, includes a high temperature/high pressure ("HTHP") fluid loss cell. In such HTHP cells, after the filter cake is established, the HTHP cell is opened to exchanged or replace the fluids in the HTHP cell, thereby releasing the temperature and pressure, from the cell. Tests are subsequently run on the replacement fluid.

Despite many valuable contributions from the art, it would be beneficial to develop improved equipment and methods for testing well fluids.

SUMMARY OF THE DISCLOSURE

In one aspect, embodiments disclosed herein relate to a well fluid test device having a cell body which includes a first end port disposed on an upper end of the cell body, a second end port disposed on a lower end of the cell body, a first lateral port disposed on a side of the cell body, and a second lateral port disposed on a side of the cell body, and a filter medium disposed in the cell body, wherein the first and second lateral ports are disposed above the filter medium.

In another aspect, embodiments disclosed herein relate to a method of evaluating a well fluid including injecting a fluid into a well fluid test device, the well fluid test device having a filter medium, heating the fluid in the well fluid test device, establishing a pressure differential across the filter medium, establishing a filter cake on the filter medium, and maintaining at least one of a temperature and a pressure in the well fluid test device.

In another aspect, embodiments disclosed herein relate to a method of evaluating a well fluid including assembling a well fluid test device having a cell body and a filter medium disposed therein, establishing a filter cake in on the filter medium, and performing at least one test sequence in the well fluid test device after establishing the filter cake while controlling at least one of a temperature and pressure of the test device.

This summary is provided to introduce a selection of concepts that are further described below in the detailed description. This summary is not intended to identify key or essential features of the claimed subject matter, nor is it intended to be used as an aid in limiting the scope of the claimed subject matter.

DETAILED DESCRIPTION

In one aspect, embodiments disclosed herein relate to test equipment for and methods of evaluating a fluid. Specifically, embodiments disclosed herein relate to test equipment and methods for simulating multiple fluid sequences for evaluating a well fluid. More specifically, embodiments disclosed herein relate to test equipment and methods for evaluating fluids during the formation and break up of a filter cake and flowback through the filter cake.

A well fluid test device and a method of evaluating a well fluid, in accordance with embodiments disclosed herein, include simulating multiple fluid sequences in a well fluid test device while maintaining at least one of a pressure and a temperature within the test device. Specifically, embodiments disclosed herein provide a test device and method for establishing a filter cake in a test device and providing a flowback procedure to determine the lift off of the filter cake from a filter medium. Additionally, embodiments disclosed herein provide a test device and method for establishing a filter cake in a test device, displacing the well fluid in the test device with a breaker fluid, and providing a flowback procedure to determine the lift off of the filter cake from a filter medium. In certain embodiments, a test device and method may also provide flowback of the well fluid and filter cake/filter cake residuals in the test device through a screen assembly. Additionally, a test device and method in accordance with the present disclosure may provide for statically establishing a filter cake or dynamically establishing a filter cake. Specifically, a filter cake may be established statically by filling the test device with fluid or injecting a fluid into the test device from above the filter medium. Alternatively, a filter cake may be established dynamically by flowing a fluid across the upper surface of the filter medium in the test device. The multiple fluid sequences may be performed sequentially without releasing temperature and/or pressure from the test device and without disturbing the established filter cake. As used herein, a well fluid may refer to a base oil, a drilling fluid, a breaker fluid, or any other fluid used in drilling or completing a well.

If desired, the temperature and/or pressure of the test device may be controllably varied during the multiple fluid sequences. However, the temperature and/or pressure may not be uncontrollably lowered or released when switching fluids entering or exiting the test device. Fluid sequences that may be performed with a test device or method of the present disclosure may include one or more of the following: breaker fluid efficiency test with flow back of filter cake or filter cake residuals; dynamic filter cake establishment below a screen and flowback of drilling fluid filter cake and a screen running fluid through the screen; dynamic filter cake establishment of drilling fluid below screen and breaker fluid efficiency test with a screen insert; dynamic filter cake establishment under a screen and placement of a gravel pack, breaker fluid efficiency test, and flowback of filter cake or filter cake residuals through the gravel pack and screen; fluid loss pill sealing capabilities and subsequent flowback of filter cake generated and well fluid; sealing capabilities of fluid loss pill towards formation through a sand control screen; flow of multiple fluids, such as displacement spacers containing surfactants and solvents, across an established filter cake for evaluating potential disturbances or non-disturbances.

Well Fluid Test Device

Figure 1A:
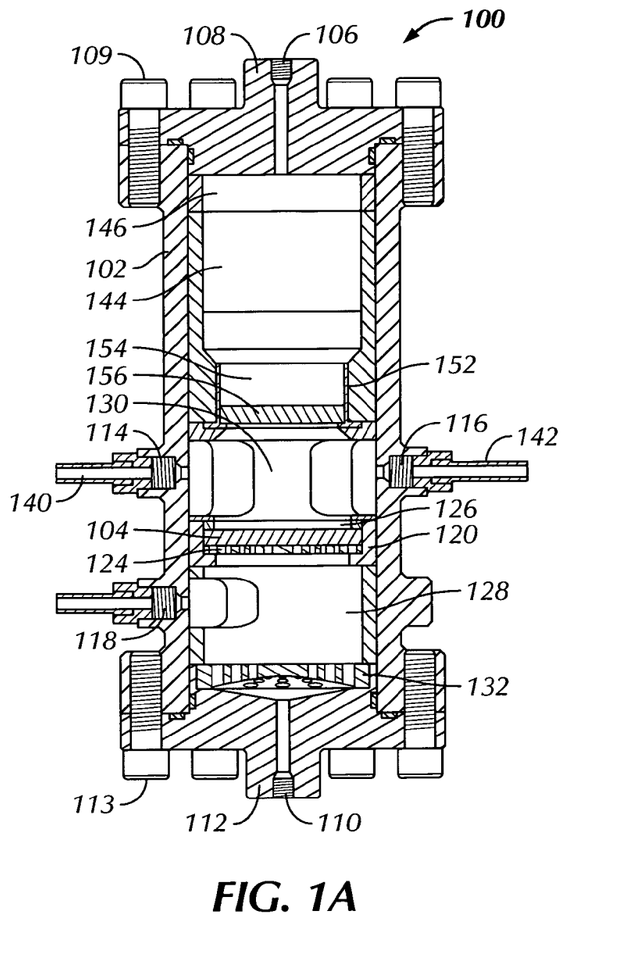
FIG. 1A is a cross-sectional view of a test device in accordance with embodiments disclosed herein.
Figure 1B:
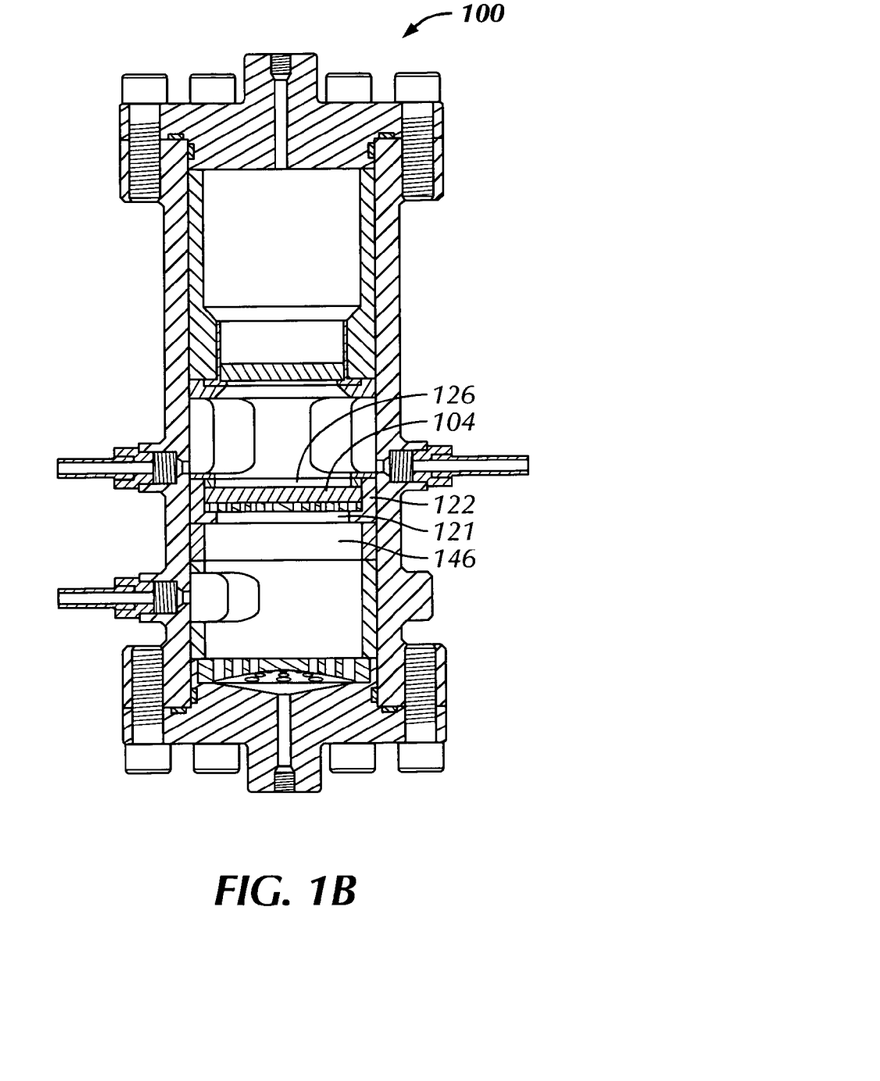
FIG. 1B is a cross-sectional view of a test device in accordance with embodiments disclosed herein.
Figure 1C:
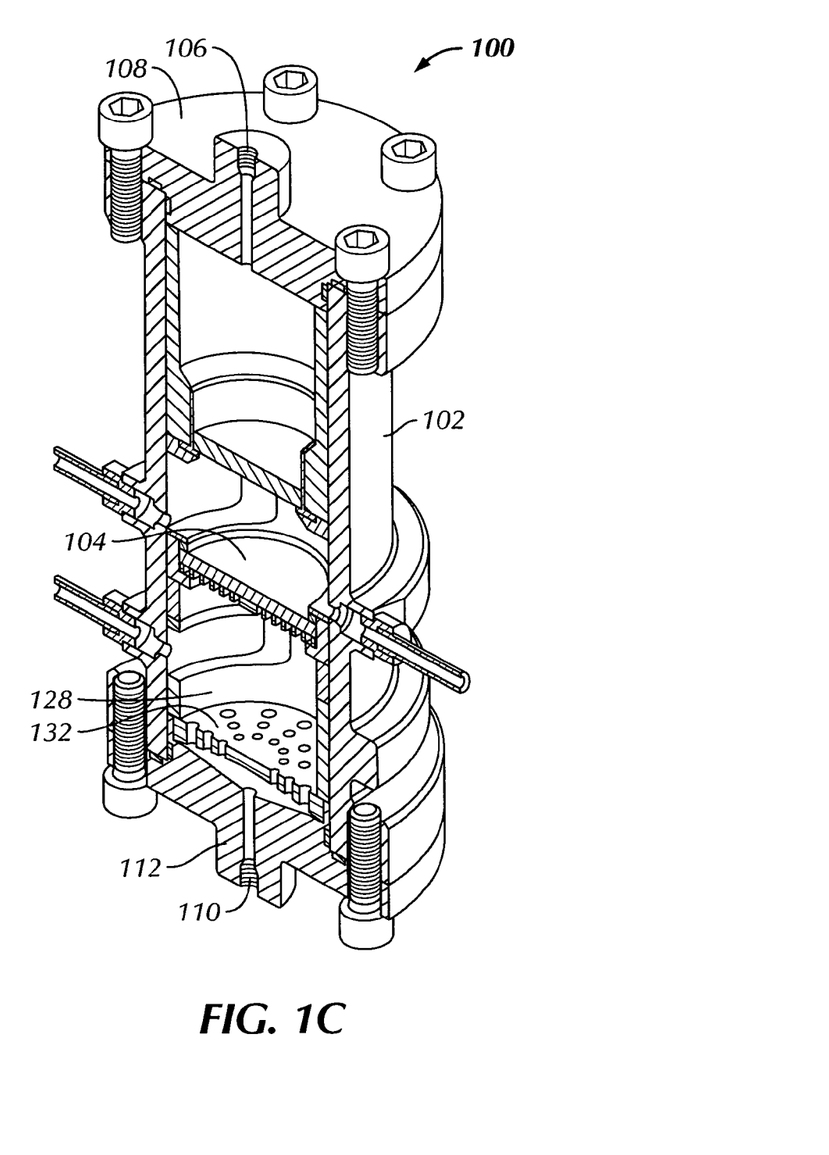
FIG. 1C is a partial perspective view of a test device in accordance with embodiments disclosed herein.

A well fluid test device in accordance with embodiments of the present disclosure includes a cell body and a filter medium disposed in the cell body. Referring to FIGS. 1A-1C, a well fluid test device 100 in accordance with embodiments of the present disclosure is shown. As shown, the test device 100 includes a cell body 102 and a filter medium 104 disposed therein. Cell body 102 may include a cylindrical housing having at least one port disposed therethrough, as discussed in detail below. The filter medium 104 may be disposed at a selected height from the top or bottom of the cell body 102 or a selected distance from one or more of the at least one port. Filter medium 104 may include any type of filter medium used to test drilling fluids including ceramic plates, polycarbonates, metallic surface filters, and fibrous filters. For example, filter medium 104 may be a ceramic disk or an aloxite disk. The filter medium 104 may be selected based on the desired permeability of the medium and the fluids to be tested. In some embodiments, the filter medium 104 may be 5 micron, 20 micron, 35 micron, or other sized mediums. Those of ordinary skill in the art will appreciate that filter medium 104 used with embodiments disclosed herein may be configured to be disposed in an impinging-flow arrangement or a surface-flow arrangement in test device 100. Impinging-flow, also known in the art as dead-end flow, refers to a fluid that flows perpendicular to a surface, and surface-flow refers to flow of a fluid parallel to a surface. According to embodiments of the present disclosure, filter medium 104 may be used in test device 100 such that a flow of fluid is perpendicular to or parallel to filter medium 104 within test device 100.

The test device 100 includes multiple ports to provide fluid communication to and from the inside of the test device 100. A first end port 106 is disposed on an upper end of the cell body 102. In some embodiments, the test device 100 may include a top end 108 coupled to the upper end of the cell body 102. The top end 108 may be coupled to the cell body 102 by any means known in the art, for example bolting, screwing, threaded engagement of the top end 108 with the cell body 102, welding, etc. For example, one or more screws 109 may be inserted through a bore in the top end 108 and threadedly engage a corresponding bore in a flange formed on the upper end of the cell body 102. The first end port 106 may be disposed in the top end 108. A second end port 110 is disposed on a lower end of the cell body 102. In some embodiments, the test device 100 may include a bottom end 112 coupled to the lower end of the cell body 102. The bottom end 112 may be coupled to the cell body by any means known in the art, for example bolting, screwing, threaded engagement of the bottom end 112 with the cell body 102, welding, etc. For example, one or more screws 113 may be inserted through a bore in the bottom end 112 and threadedly engage a corresponding bore in a flange formed on the lower end of the cell body 102. The second end port 110 may be disposed in the bottom end 112.

Figure 2:
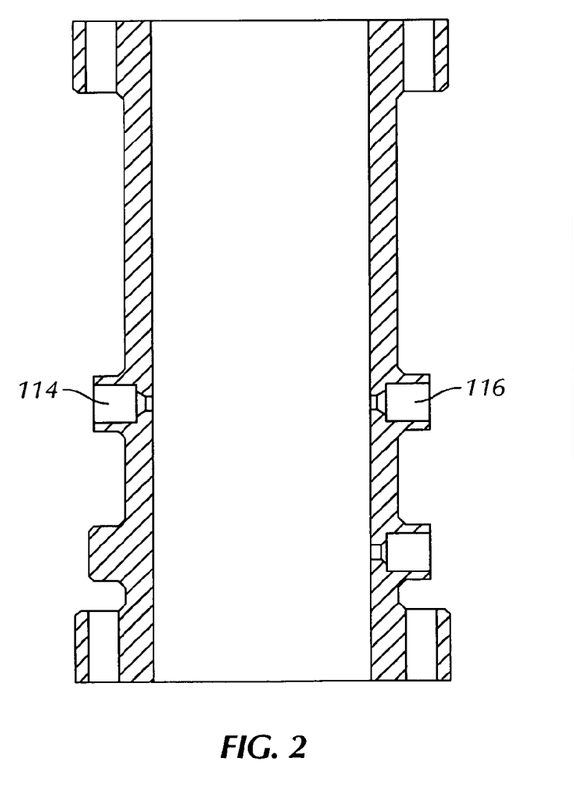
FIG. 2 is a cross-sectional view of a cell body of a test device in accordance with embodiments disclosed herein.

The test device 100 further includes at least one lateral port. The test device may include one lateral port, two lateral ports, three lateral ports, or more to facilitate fluid flow in and out of the test device 100. As shown in FIG. 1A, test device 100 may include a first lateral port 114 disposed on a side of the cell body 102. The first lateral port 114 is disposed axially above the filter medium 104 disposed in the cell body 102. Test device 100 may also include a second lateral port 116 disposed on a side of the cell body 102. The second lateral port 116 is disposed axially above the filter medium 104 disposed in the cell body 102. In some embodiments, the second lateral port 116 may be disposed directly opposite the first lateral port 114. In other words, the second lateral port 116 may be axially aligned with and circumferentially opposite the first lateral port 114, as shown in FIG. 2. In other embodiments, the second lateral port 116 may be azimuthally disposed from the first lateral port 114. Further, in some embodiments, the first and lateral ports 114, 116 may be axially aligned, while in other embodiments, the first and lateral ports 114, 116 may be axially offset.

A third lateral port 118 may be disposed on a side of the cell body 102, disposed axially below the filter medium 102 disposed in the cell body 102. The third lateral port 118 may be circumferentially aligned with the first or second lateral ports 114, 116 or circumferentially misaligned with the first or second lateral ports 114, 116. The third lateral port 18 may be disposed a selected axial distance from the first and/or second lateral ports 114, 116. The axial distance between the third lateral port 118 and the first and/or second lateral ports 114, 116 may be selected based on, for example, the type of fluid sequences to be performed with the test device 100, the type of fluid(s) to be tested with the test device 100, the type of filter medium 104 used.

The test device 100 may further include a filter medium holder ring 120 disposed in the cell body 102 and configured to receive the filter medium 104. The filter medium holder ring 120 may include a cylindrical body 121 with a bore therethrough and at least a lower lip 122. In some embodiments, the filter medium holder ring 120 may also include an upper lip (not shown). The lower lip 122 and/or the upper lip (not shown) may be integrally formed with the cylindrical body 121 or may be separately coupled to the cylindrical body 121 by any means known in the art, for example, mechanical fasteners, welding, or adhesives. The filter medium holder ring 120 may be installed within the test device 100 and supported by one or more spacer rings, discussed in more detail below. A filter medium support 124 may be disposed in the filter medium holder ring 120 on the lower lip 122. The filter medium 104 may then be disposed on the filter medium support 124. In some embodiments, the filter medium support 124 may be a flat plate formed from composite, stainless steel, metals, or alloys and is configured to structurally support the filter medium 104 during the multiple fluid sequences performed to test one or more well fluids in the test device 100. The plate of the filter medium support 124 may be perforated or include a plurality of openings therethrough to allow for fluid flow across the filter medium support 124. In other embodiments, the filter medium support 124 may be a coarse mesh layer that provides rigidity and structural support for the filter medium 104. A lock ring 126 may be disposed axially above the filter medium 104 and within the filter medium holder ring 120 to secure the filter medium 104 within the filter medium holder ring 120 as fluid is flowed from above and/or below the filter medium 104. The lock ring 126 may be coupled to the filter medium holder ring 120 by any means known in the art, for example, threaded connections, mechanical fasteners, press-fit, etc.

The test device 100 further includes a first spacer ring 128 disposed below the filter medium 104 and a second spacer ring 130 disposed above the filter medium. The first spacer ring 128 is configured to abut an inner surface of bottom end 112 or a diverter 132, discussed in more detail below. A lower surface of the filter medium holder ring 120 may abut the upper surface of the first spacer ring 128, such that the first spacer ring 128 supports the filter medium holder ring 120 and filter medium 104. The height of the first spacer ring 128 may, therefore, be selected so as to properly align the filter medium 104 at a preselected distance between the third lateral port 118 and the first and second lateral ports 114, 116 or the upper and lower ends of the cell body 102.

Figure 3:
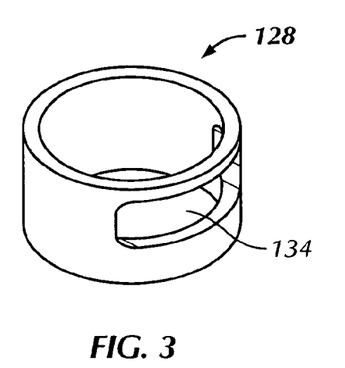
FIG. 3 is a perspective view of a spacer ring in accordance with embodiments disclosed herein.

As shown in more detail in FIG. 3, first spacer ring 128 is a cylindrical ring and includes an opening 134 through a wall of the ring. Referring back to FIGS. 1A-1C, the opening 134 of the first spacer ring 128 allows for fluid communication between the third lateral port 118 and inside the cell body 102. As shown, the opening 134 is axially and circumferentially aligned with the third lateral port 118. One of ordinary skill in the art will appreciate that first spacer ring 128 may include one opening, two openings, or more openings to accommodate one or more ports in the lower end of the cell body 102.

Figure 4:
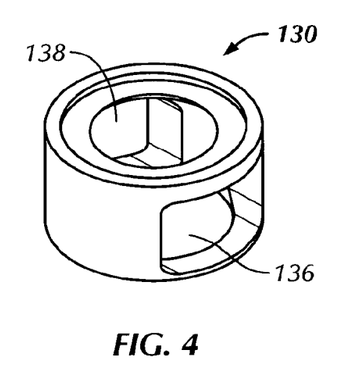
FIG. 4 is a perspective view of a spacer ring in accordance with embodiments disclosed herein.

A bottom surface of the second spacer ring 130 may abut an upper surface of the filter medium holder ring 120. The second spacer ring 130 is a cylindrical ring having at least one opening through a wall of the ring configured to align with at least one port in the cell body 102 disposed above the filter medium 104. As shown in FIG. 4, the second spacer ring 130 may include a first opening 136 and a second opening 138. Referring back to FIGS. 1A-1C, first opening 136 axially and circumferentially aligns with first lateral port 114 to provide fluid communication between a fluid line 140 connected to the first lateral port 114 and the cell body 102. Similarly, second opening 138 is axially and circumferentially aligned with second lateral port 116 to provide fluid communication between a fluid line 142 and the cell body 102.

Figure 5:
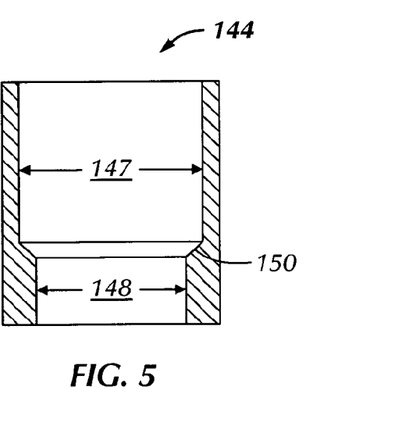
FIG. 5 is a cross-sectional view of an inner body of a test device in accordance with embodiments disclosed herein.

An inner body 144 having a main body, for example, a cylindrical body with a bore therethrough, is disposed above the second spacer ring 130 in the cell body 102. A lower surface of the inner body 144 may abut an upper surface of the second spacer ring 130 and an upper surface of inner body 144 may abut a lower surface of top end 108. In some embodiments, the upper surface of the inner body 144 may abut a lower surface of a third spacer ring 146 disposed above the inner body 144, as described below. As shown in more detail in FIG. 5, inner body 144 may include a first inner diameter 147 and a second inner diameter 148. The first inner diameter 147 is larger than the second inner diameter 148, forming a shoulder 150 therebetween. One of ordinary skill in the art will appreciate that the shoulder may be an angled surface, for example, 5 degrees, 30 degrees, 45 degrees, 60 degrees or may be a right angle.

Referring back to FIGS. 1A-1C, when a screen test of a well fluid is to be performed to evaluate sand control during one of the multiple fluid sequences described below, a screen assembly 152 may be disposed within the inner body 144. In one embodiment, for example, the screen assembly 152 may be disposed in a lower end (e.g., in a portion of the inner body 144 having the second diameter 148 (FIG. 5)) of the inner body 144. The screen assembly may include a screen holder 154 disposed within the lower end of the inner body 144 and a screen 156 disposed within the screen holder 154. The screen 156 may include a sand control screen or a portion of sand control screen. The screen 156 may include, for example, a wire mesh, a slotted or perforated metal sheet, or a wire-wrapped screen (i.e., a slotted or perforated metal sheet wrapped with wire). The screen 156 may be coupled to the screen holder 154 by any means known in the art, for example, by clamping, welding, or mechanically fastening.

In some embodiments, the third spacer ring 146, or fixed distance ring, may be provided to allow proper alignment of the filter medium 104 within the cell body 102. The third spacer ring 146 may include a cylindrical body having a bore therethrough. Specifically, the relative location of the filter medium 104 with respect to the ports 114, 116, 118, 106, 110 may be adjusted by inserting a third spacer ring 146 in a selected location in the test device 100. For example, as shown in FIG. 1A, the third spacer ring 146 may be disposed above the inner body 144. In this embodiment, the filter medium 104 is positioned a selected distance below the first and second lateral ports 114, 116.

In another embodiment, as shown in FIG. 1B, the third spacer ring 146 may be disposed above the first spacer ring 128 and below the filter medium holder ring 120. When the third spacer ring 146 is positioned as shown in FIG. 1B, the filter medium 104 is disposed just below the first and second lateral ports 114, 116. The fluid flowed in and out of the test device 100 through the first and second lateral ports 114, 116 is, therefore, in close proximity to the upper surface of the filter medium 104. As such, a surface-flow arrangement is provided.

The height of the third spacer ring 146 may be selected based on the desired location of the filter medium 104 within the test device. For example, if a well fluid test in accordance with embodiments disclosed herein establishes a dynamic filter cake, then a surface-flow arrangement may be provided to allow flow from the first lateral port 114 to the second lateral port 116 proximate to the filter medium 104, which will be discussed in more detail below. In this example, the third spacer ring 146 may be positioned as shown in FIG. 1B. If, however, an impinging-flow arrangement is required, as for example in establishing a static filter cake, the third spacer ring 146 may be positioned as shown in FIG. 1A. One of ordinary skill in the art will appreciate some test devices 100 in accordance with embodiments disclosed herein do not include a third spacer ring.

In other embodiments, a third spacer ring 146 and a fourth spacer ring (not shown), similarly formed as the third spacer ring 146, may be provided. In this embodiment, the third spacer ring 146 may be provided above the inner body 144 and the fourth spacer ring (not shown) may be provided between the first spacer ring 128 and the filter medium holder ring 120, or vice versa. The third spacer ring 146 and fourth spacer ring (not shown) may have the same height or may be of different heights. Furthermore, while FIGS. 1A and 1B show the third spacer 146 disposed above the inner body 144 and between the first spacer ring 128 and the filter medium holder ring 120, respectively, the third spacer ring 146 may be disposed in other locations without departing from the scope of embodiments disclosed herein. For example, the third spacer ring 146 may be disposed between the second spacer ring 130 and the inner body 144 or below the first spacer ring 128.

As mentioned above, test device 100 may further include a diverter 132. The diverter 132 is disposed in the cell body 102 below the filter medium 104. In some embodiments, the diverter 132 may be disposed below the first spacer ring 128. The diverter 132 is configured to distribute a flow of fluid from second end port 110 during a flowback fluid sequence, described in more detail below. Specifically, diverter 132 may provide an even distribution of fluid flowing from second end port 110. Distribution of a fluid through the diverter 132 may provide more uniform lift off of a filter cake established on the upper surface of the filter medium 104.

As shown in FIGS. 1A-1C, diverter 132 may include a plate having a plurality of openings therethrough. An upper surface of the diverter 132 may be flat, while a lower surface of the diverter 132 may be concave. The plurality of openings may be radially arranged as shown in FIG. 1C. In other embodiments, the plurality of openings may be arranged in a staggered manner or in any other arrangement. The size of each opening may vary. For example, as shown in FIG. 1C, the diameter of the openings close to the center of the diverter 132 may be smaller than the diameter of the openings close to the outer edge of the diverter 132. In other embodiments, the size (diameter) of the openings may be constant.

The height of each of the components of the test device 100, e.g., spacer rings 128, 130, 146, inner body 144, filter medium holder ring 120, diverter 132, is selected such that that the total sum of the heights provides for a fully stacked assembly within the cell body 102, such that each of the components is securely installed within the cell body 102.

System

Figure 6:
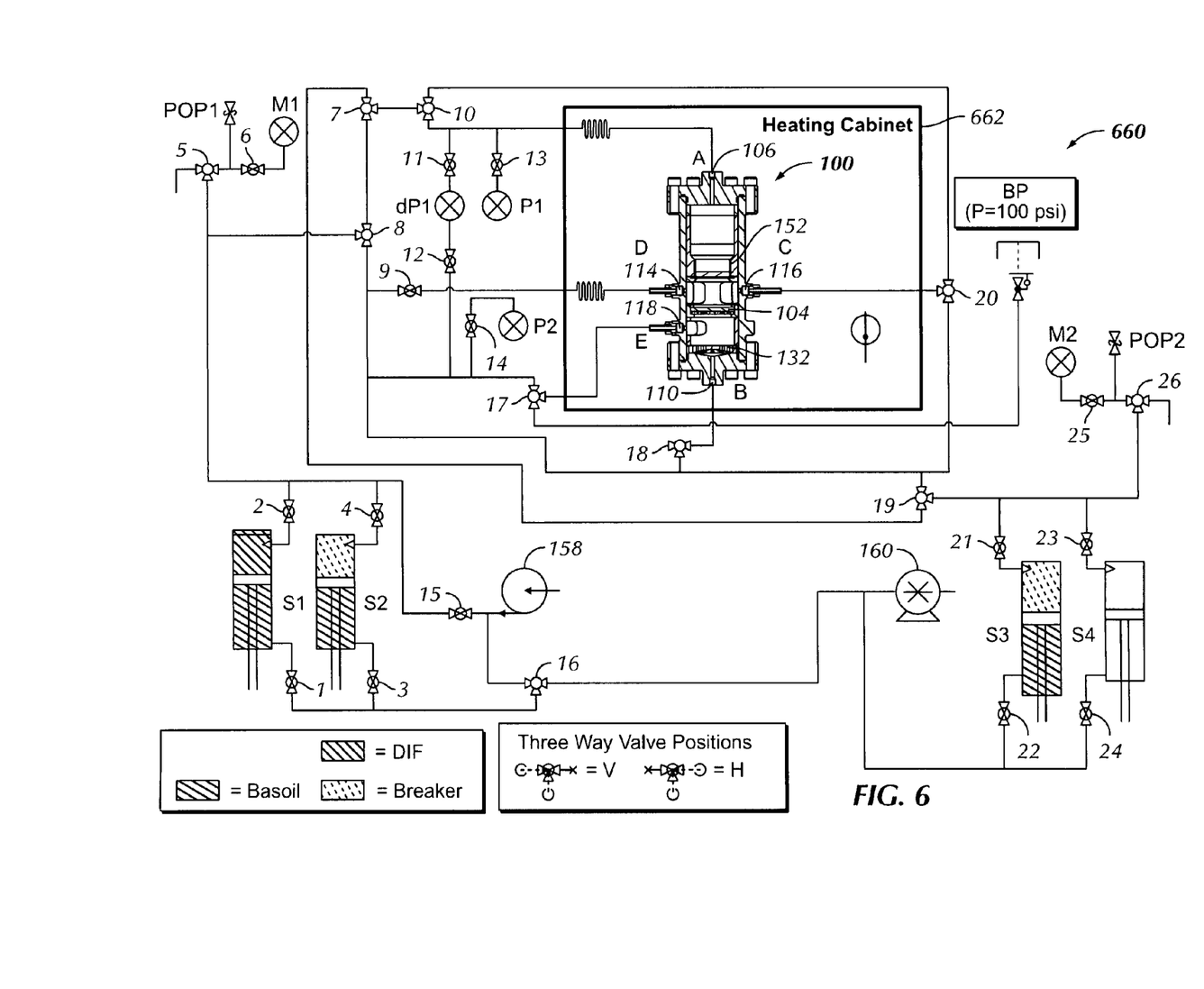
FIG. 6 is a process and instrumentation diagram of a system for testing a well fluid in accordance with embodiments disclosed herein.
Figure 7:
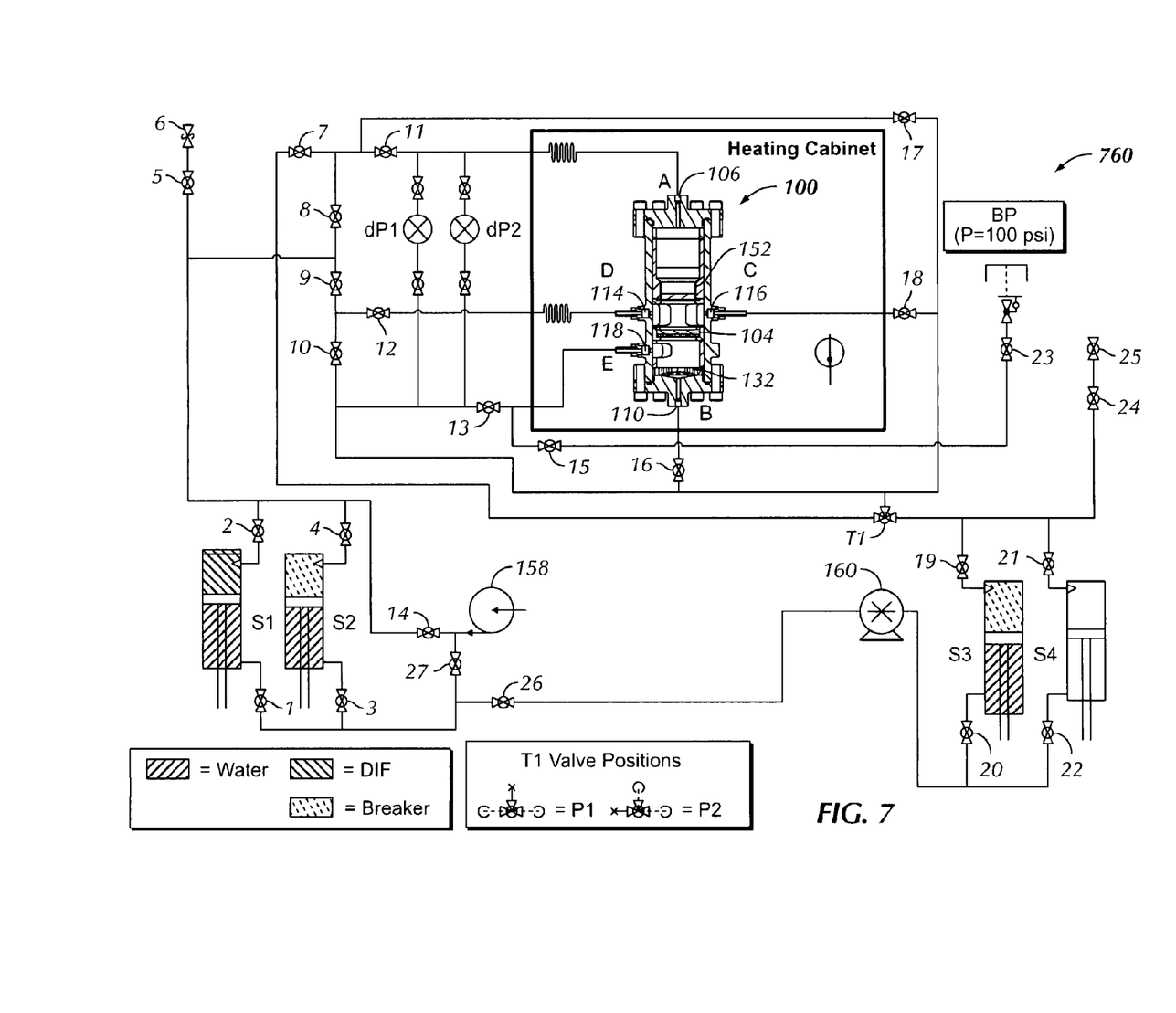
FIG. 7 is a process and instrumentation diagram of a system for testing a well fluid in accordance with embodiments disclosed herein.

A test device as described herein may be used in a system for simulating multiple fluid sequences for evaluating one or more well fluids. As shown in FIGS. 6 and 7, well fluid evaluation systems 660, 760 in accordance with embodiments disclosed herein include test device 100 as described above with reference to FIGS. 1-5. The well fluid evaluation system 660, 760 further includes one or more fluid storage vessels. The well fluid evaluation system 660, 760 may include, for example, four fluid cylinders S1, S2, S3, and S4. One of ordinary skill in the art will appreciate that one, two, three, four, or more cylinders may be used to store one or more fluids for use in evaluating at least one well fluid. In one embodiment, one or more of the cylinders S1, S2, S3, S4 may include a piston separating a first fluid from a second fluid within the cylinder. The first and second fluid may be different fluids or may be the same fluid.

The well fluid evaluation system 660, 760 further includes a piping network comprised of one or more pieces of pipe connecting the cylinders S1, S2, S3, S4 to the test device 100. As used herein, piping network may include metal tubulars, hoses, lines, piping, and any other fluid communication means. One or more valves are disposed in line with the piping network to direct fluid to various locations within the system, including to the test device 100, the cylinders S1, S2, S3, S4, pressure gages, temperature gages, flow meters, etc. The valves used in the well fluid evaluation system 660, 760 may be any valve known in the art, for example, three-way valves, gate valves, globe valves, check valves, etc. Different sections of pipe may each be connected to test device 100 through a port on the test device 100 to provide fluid communication between the cylinders S1, S2, S3, S4 and the test device 100. Specifically, sections of the piping network are fluidly connected to first end port 106, second end port 110, first lateral port 114, second lateral port 116, and third lateral port 118.

The well fluid evaluation system 660, 760 further includes at least one pump to direct the fluid through the piping network and to increase pressure contained within the test device 100. In some embodiments two or more pumps may be used to pump fluids through the system 660, 760 and apply pressure within the test device 100. A first pump 158 in accordance with embodiments disclosed herein may include, for example, centrifugal pumps, rotary vane pumps, piston pumps, etc. In one embodiment, the well fluid evaluation system 660, 760 may include a reciprocating pump, for example, a 333 pump, commercially available from Gilson, Inc. (Middleton, Wis.). The well evaluation system 660, 760 may also include a second pump 160 which may include a non-pulsating pump. For example, a multi-cylinder pump, such as, a Quizix QX-1500 pump, commercially available from Vindum Engineering, Inc. (San Ramon, Calif.). Using the piping network and various valves discussed above, the first and second pumps 158, 160 may be connected in series, parallel, or independent from one another. Further, first and second pumps 158, 160 may provide pump fluid through the same or different ports within the test device 100.

The well fluid evaluation system 660, 760 further includes a heating cabinet 662, 762. The test device 100 may be placed within the heating cabinet 662, 762. The heating cabinet 662, 762 may include one or more openings (not shown) to allow one or more lines of the piping network to be inserted therethrough and connected to the test device 100. Seals (not shown) may be provided within the openings to seal around the piping lines to maintain a desired temperature within the heating cabinet. In other embodiments, a heating jacket (not shown) may be disposed around the test device 100 without the need for heating cabinet 662, 762. The heating cabinet 662, 762 or heating jacket may include a heating element (not shown) connected to a control system (not shown) such that the temperature applied to the test device 100 may be controlled. In other embodiments, a fluid flowing to the test device 100 may be heated before the fluid enters the test device 100. For example, a fluid heater may be disposed proximate a portion of the piping network, such that the fluid is heated as it flows through the pipelines in advance of entering the test device 100.

Operation

Methods of evaluating a well fluid in accordance with embodiments of the present disclosure will now be described. FIGS. 6 and 7 show process and instrumentation diagrams of systems 660, 760 used in accordance with embodiments of the present disclosure for evaluating a fluid, where like numbers represent like features. As shown in FIGS. 6 and 7 and as discussed above, test device 100 having the features described above with reference to FIGS. 1-5 may be used to evaluate a well fluid in accordance with embodiments disclosed herein.

A method of evaluating a well fluid in accordance with embodiments disclosed herein may include one or more fluid sequences performed within test cell 100. The fluid sequences may be performed sequentially. In some embodiments, a predetermined period of time may be provided between sequences. Fluid sequences that may be performed with test device 100 may include one or more of the following: breaker fluid efficiency test with flow back of filter cake or filter cake residuals; dynamic filter cake establishment below a screen and flowback of drilling fluid filter cake and a screen running fluid through the screen; dynamic filter cake establishment of drilling fluid below screen and breaker fluid efficiency test with a screen insert; dynamic filter cake establishment under a screen and placement of a gravel pack, breaker fluid efficiency test, and flowback of filter cake or filter cake residuals through the gravel pack and screen; fluid loss pill sealing capabilities and subsequent flowback of filter cake generated and well fluid; sealing capabilities of fluid loss pill towards formation through a sand control screen; flow of multiple fluids, such as displacement spacers containing surfactants and solvents, across an established filter cake for evaluating potential disturbances or non-disturbances.

While switching between fluid sequences, at least one of a temperature and pressure within the test device 100 may be maintained. Specifically, as the fluid flowed to the test device 100 changes (e.g., type of fluid flowed to the test device, direction of fluid flowed to the test device, ports that are opened or closed to accommodate flow to or from the test device, etc), the pressure and/or temperature within the test device 100 may be controlled. For example, the temperature of the test device 100 is maintained or may be controllably adjusted to ensure the temperature of the fluid within the test device 100 remains constant or to ensure that the temperature may be quickly adjusted to a desired temperature. Accordingly, during fluid sequence changes, the previously gained by the fluid within the test device is not lost. Additionally, the pressure applied to the test device 100 during a fluid sequence is not released as a second sequence is performed. The pressure within the test device 100 may remain constant between sequences or may be variably controlled. The various fluid sequences are described in detail below.

Referring to FIGS. 6 and 7, a method of evaluating a well fluid includes injecting a fluid into test device 100 having filter medium 104. The well fluid may be injected from one of cylinders S1, S2, S3, S4 into the test device 100 through first end port 106. Alternatively, a fluid may be injected from one of the cylinders S1, S2, S3, S4 into the test device 100 through second end port 110. The fluid may be a base oil, a well fluid, such as a drilling fluid, formation fluids, hydrocarbons, and/or water. In one embodiment, the test device 100 may be fully filled with base oil. In some embodiments, a predetermined amount of base oil may be flowed into the test device 100 and a drilling fluid may be subsequently added to the test device 100 to fill the test device 100. For example, the test device may be filled with base oil up to the top of filter medium 104, and a drilling fluid may be injected into the test device above the base oil to fill the test device 100. The well fluid may be injected into the test device 100 using first pump 158, second pump 160, or the well fluid may be placed in the test device 100 before the top end 108 and/or bottom end 112 is assembled to the cell body 102. The lines of the piping network may be flushed with base oil.

Establishing a Static Filter Cake

To establish a static filter cake on filter medium 104, a drilling fluid is injected into the well fluid test device. For example, the drilling fluid may be injected through first end port 106 of test device 100. In one embodiment, first pump 158 may be used to pump drilling fluid into the test cell 100. In other embodiments, second pump 160 (i.e., a non-pulsating pump) may be used to bleed drilling fluid through the piping network into the test device 100 through first end port 106. Valves fluidly connecting the piping network to the remaining ports of the test device are closed. In other words, valves connecting first, second, and third lateral ports 114, 116, 118, and second end port 110 from the piping network are closed.

The test device 100 is then heated with, for example heating cabinet 662, 762. The fluid within the test device 100 may be heated to an initial predetermined temperature. For example, in some embodiments, the fluid within test device 100 may be heated to 176° F. (80° C.), 212° F. (100° C.), or 356° F. (180° C.). One of ordinary skill in the art will appreciate that the predetermined temperature may be determined based on, for example, expected well conditions, the fluid sequences to be performed, the fluids to be tested, etc. As the drilling fluid is heated, the drilling fluid expands and air is allowed to escape out of the test device 100 through a valve (not shown), for example, a relief valve.

Pressure within test device 100 is then increased. For example, the pressure within the test device 100 may be increased to 150 to 200 psi. First or second pumps 158, 160 may be used to pressurize test device 100. The temperature of the fluid within test device 100 may then be increased to a predetermined test temperature. Specifically, the temperature may be increased to a desired test parameter. For example, the temperature may be increased from 176° F. (80° C.) to 212° F. (100° C.), or 356° F. (180° C.). The test device may then be left for a predetermined amount of time. For example, the test device 100 may be allowed to stand for 30 minutes, 1 hour, 4 hours, etc. The second pump 160 may allow for a volume of drilling fluid from within the test device 100 to return to one of the cylinders, i.e., retract, due to heat expansion within the test device 100.

A pressure differential across filter medium 104 may then be established by increasing a fluid pressure applied to the test device 100 above filter medium 104 to a desired pressure or overbalanced pressure, and maintaining a constant pressure below filter medium 104. For example, first pump 158 may be used to pressurize the test device through first end port 106 to a pressure of 600 psi, while second pump 160 may be used to provide a constant pressure of 100 psi through second end port 110 or third lateral port 118. Thus, a pressure differential of 500 psi is established and maintained by first and second pumps 158, 160 across the filter medium 104. The pressure differential is adjustable by adjusting the pressure applied by one or both of first and second pumps 158, 160. One of ordinary skill in the art will appreciate that various pressure differential may be applied across the filter medium 104. For example, a pressure differential of 300 psi, 800 psi, 1,000 psi, or 1,500 psi may be desirable.

Due to the temperature and pressure applied to the well fluid contained within the test device 100, a filter cake (not shown) is established on the filter medium 104. Temperature and pressure gages may be used to monitor the temperature of the fluid in the test device 100 and the pressure differential across the filter medium 104. A volume of fluid pumped into the test device 100 is monitored with respect to time and pressure change to determine the amount of time required to establish the filter cake. Based on the monitoring, once a determination is made that the filter cake is formed, first and second pumps 158, 160 are turned off.

Displacing Drilling Fluid to Breaker Fluid

To displace the drilling fluid from above the filter medium 104 and replace the drilling fluid with a breaker fluid, valves in communication with a first cylinder (e.g., S1) housing the drilling fluid are closed, and valves in communication with a second cylinder (e.g., S2) housing a breaker fluid are opened. The first pump 158 may be used to pump the breaker fluid from the second cylinder to first end port 106 at a desired rate. For example, the first pump 158 may supply breaker fluid at a rate of 10 ml/min, 25 ml/min, 50 ml/min, 100 ml/min, 200 ml/min, 300 ml/min, or any other desired or predetermined rate. As breaker fluid is pumped in through the first end port 106, at least one lateral port above the filter medium 104 is opened to allow for the drilling fluid within the test device 100 to be removed from the test device 100. In one embodiment, valves in fluid communication with first and second lateral port 114, 116 may be alternatingly opened and closed to allow drilling fluid to exit the test device 100 through the first and second lateral ports 114, 116. In some embodiments, the valves in fluid communication with first and second lateral port 114, 116 may be opened simultaneously. In other embodiments, the valves in fluid communication with first and second lateral port 114, 116 may be opened and closed alternatingly and then opened simultaneously. In yet other embodiments, first end port 106 may be closed, breaker fluid may be pumped in through first lateral port 114, and the drilling fluid may be displaced through second lateral port 116. To maintain a temperature of the fluid within the test device 100, the breaker fluid may be heated before entering the test device 100 to a temperature approximately equal to the desired or set temperature of heating cabinet 662, 762. For example, the breaker fluid (or other fluids entering the test device) may be preheated by a heater, coiled tubing for increased friction, etc.

The second pump 160 may provide a constant pressure to the fluid below the filter medium 104. The pressure applied by the first pump 158 to the fluid above the filter medium 104 and the pressure applied by the second pump 160 to the fluid below the filter medium 104 may be approximately equal, such that the pressure differential across the filter medium is approximately zero. For example, the pressure applied by the first and second pumps 158, 160 may be approximately 300 psi, 600 psi, 900 psi, etc.

Once a desired volume of breaker fluid (e.g., a volume of the test device 100 above the filter medium 104 or greater) has been pumped into the test device 100), the valves in fluid communication with first and second lateral port 114, 116 are closed and the first pump 100 is stopped. The second pump 160 is adjusted to maintain a constant pressure below the filter medium 104. For example, second pump 160 may maintain a constant pressure of 50 psi, 100 psi, 200 psi, etc. If desired, the second pump 160 may maintain the constant pressure for a desired amount of time to provide a breaker shut-in, i.e., to allow the breaker fluid to penetrate the filter cake. For example, the second pump 160 may maintain constant pressure below the filter medium 104 for 15 mins, 30 mins, 45 mins, 1 hour, etc. Fluid may be allowed to bleed out of test device 100 through a relief valve. Subsequently, the constant pressure applied by the second pump 160 may be removed and the pressure decline below the filter medium 104 may be monitored. For example, a valve in fluid connection with the third lateral port 118 may be positioned to redirect flow from between the second pump 160 and the third lateral port 118 to between the third lateral port 118 and a pressure gage P2, which provides a pressure reading for the pressure of the fluid below the filter medium 104. A pressure gage P1 provides a reading for the fluid pressure above the filter medium 104. The rate at which the pressure equalizes across the filter cake on the filter medium 104 (i.e., rate at which P1 and P2 equalize) is monitored.

Flowback

Once the breaker fluid sequence has been performed, a flowback sequence may be performed to determine a lift-up pressure, i.e., a pressure at which the filter cake or filter cake residuals is lifted off the filter medium 104. Valves in fluid communication with first, second, and third lateral ports 114, 116, 118 are closed and second end port 110 is opened and in fluid communication with pump 158. Pump 158 pumps a flowback fluid, for example, base oil, formation fluid, or water, from one of the cylinders through second end port 110. The flowback fluid is pumped at a constant, low rate of, for example, 5 ml/min, 10 ml/min, 25 ml/min, 50 ml/min, or any other desired or predetermined rate. The pressures of the fluids above and below the filter medium 104 are measured by pressure gages P1, P2, or differential pressure gage dP1, and monitored over time to determine lift up pressure of the filter cake.

In one embodiment, the flowback fluid flows through second end port 110, up through diverter 132, and through filter medium 104. Diverter 132 diverts the flow of flowback fluid from second end port 110 and disperses or evenly distributes the flow of fluid to the filter medium 104. By distributing the flowback fluid flowing against the filter medium 104, the diverter helps provide a flow of flowback fluid that will allow for more uniform lift off of the filter cake from the filter medium.

Establishing a Dynamic Filter Cake

To establish a dynamic filter cake on filter medium 104, a drilling fluid is injected into the well fluid test device and flowed across the surface of the filter medium 104. The drilling fluid may be injected through first lateral port 114 of test device 100. First pump 158 may be used to pump drilling fluid into the test cell 100. Second lateral port 116 is opened to allow the drilling fluid above the filter medium 104 to exit the test cell 100 as drilling fluid is pumped in through first lateral port 114. Valves fluidly connecting the piping network to the remaining ports of the test device are closed. In other words, valves connecting third lateral port 118, and first and second end ports 106, 110 to the piping network are closed.

The test device 100 is then heated with, for example heating cabinet 662, 762. The fluid within the test device 100 may be heated to an initial predetermined temperature. For example, in some embodiments, the fluid within test device 100 may be heated to 176° F. (80° C.), 212° F. (100° C.), or 356° F. (180° C.). One of ordinary skill in the art will appreciate that the predetermined temperature may be determined based on, for example, expected well conditions, the fluid sequences to be performed, the fluids to be tested, etc.

As the drilling fluid is heated, the drilling fluid expands and air is allowed to escape out of the test device 100 through a valve (not shown), for example, a relief valve.

Pressure within test device 100 is then increased. For example, the pressure within the test device 100 may be increased to 150 to 200 psi. First or second pumps 158, 160 may be used to pressurize test device 100. The temperature of the fluid within test device 100 may then be increased to a predetermined test temperature. Specifically, the temperature may be increased to a desired test parameter. For example, the temperature may be increased from 176° F. (80° C.) to 212° F. (100° C.), or 356° F. (180° C.). The test device may then be left for a predetermined amount of time. For example, the test device 100 may be allowed to stand for 30 minutes, 1 hour, 4 hours, etc. The second pump 160 may allow for a volume of drilling fluid from within the test device 100 to return to one of the cylinders, i.e., retract, due to heat expansion within the test device 100.

A pressure differential across filter medium 104 may then be established by increasing a fluid pressure applied to the test device 100 above filter medium 104 to a desired pressure or overbalanced pressure, and maintaining a constant pressure below filter medium 104. For example, first pump 158 may be used to pressurize the test device through first lateral port 114 to a pressure of 600 psi, while second pump 160 may be used to provide a constant pressure of 100 psi through second end port 110 or third lateral port 118. Thus, a pressure differential of 500 psi is established and maintained by first and second pumps 158, 160 across the filter medium 104. The pressure differential is adjustable by adjusting the pressure applied by one or both of first and second pumps 158, 160. One of ordinary skill in the art will appreciate that various pressure differential may be applied across the filter medium 104. For example, a pressure differential of 300 psi, 800 psi, 1,000 psi, or 1,500 psi may be desirable.

Due to the temperature and pressure applied to the well fluid contained within the test device 100 and the surface-flow arrangement of the first and second lateral ports 114, 116 and the filter medium 104, a dynamic filter cake (not shown) is established on the filter medium 104. Temperature and pressure gages may be used to monitor the temperature of the fluid in the test device 100 and the pressure differential across the filter medium 104. A volume of fluid pumped into the test device 100 is monitored with respect to time and pressure change to determine the amount of time required to establish the filter cake. Based on the monitoring, once a determination is made that the filter cake is formed, first and second pumps 158, 160 are turned off.

Displacing Drilling Fluid to Screen Running Fluid and Flowback

As discussed above with reference to the test device 100 in FIGS. 1-5, in certain embodiments a screen assembly may be installed in a test device 100 in accordance with embodiments of the present disclosure to evaluate sand control installment in a well fluid.

To displace the drilling fluid from above the filter medium 104 and replace the drilling fluid with a screen running fluid (e.g., low solids or conditioned drilling fluid), valves in communication with a first cylinder (e.g., S1) housing the drilling fluid are closed, and valves in communication with a second cylinder (e.g., S2) housing a screen running fluid are opened. The first pump 158 may be used to pump the screen running fluid from the second cylinder to first end port 106 at a desired rate. For example, the first pump 158 may screen running fluid at a rate of 10 ml/min, 25 ml/min, 50 ml/min, 100 ml/min, 200 ml/min, 300 ml/min, or any other desired or predetermined rate. As screen running fluid is pumped in through the first end port 106, at least one lateral port above the filter medium 104 is opened to allow for the drilling fluid within the test device 100 to be removed from the test device 100. In one embodiment, valves in fluid communication with first and second lateral port 114, 116 may be alternatingly opened and closed to allow drilling fluid to exit the test device 100 through the first and second lateral ports 114, 116. In some embodiments, the valves in fluid communication with first and second lateral port 114, 116 may be opened simultaneously. In other embodiments, the valves in fluid communication with first and second lateral port 114, 116 may be opened and closed alternatingly and then opened simultaneously. In yet other embodiments, first end port 106 may be closed, screen running fluid may be pumped in through first lateral port 114, and the drilling fluid may be displaced through second lateral port 116 and then exit through first end port 106 by pumping in through first lateral port 114 and then second lateral port 116, alternatingly. To maintain a temperature of the fluid within the test device 100, the screen running fluid may be heated before entering the test device 100 to a temperature approximately equal to the desired or set temperature of heating cabinet 662, 762. For example, the screen running fluid (or other fluids entering the test device) may be preheated by a heater, coiled tubing for increased friction, etc.

The second pump 160 may provide a constant pressure to the fluid below the filter medium 104. The pressure applied by the first pump 158 to the fluid above the filter medium 104 and the pressure applied by the second pump 160 to the fluid below the filter medium 104 may be approximately equal, such that the pressure differential across the filter medium is approximately zero. For example, the pressure applied by the first and second pumps 158, 160 may be approximately 300 psi, 600 psi, 900 psi, etc.

Once a desired volume of screen running fluid (e.g., a volume of the test device 100 above the filter medium 104 or greater) has been pumped into the test device 100), the valves in fluid communication with first and second lateral port 114, 116 are closed and the first pump 100 is stopped. The second pump 160 is adjusted to maintain a constant pressure below the filter medium 104. For example, second pump 160 may maintain a constant pressure of 50 psi, 100 psi, 200 psi, etc. If desired, the second pump 160 may maintain the constant pressure for a desired amount of time. For example, the second pump 160 may maintain constant pressure below the filter medium 104 for 15 mins, 30 mins, 45 mins, 1 hour, etc. Fluid may be allowed to bleed out of test device 100 through a relief valve.

A flowback sequence may then be performed to determine a lift-up pressure, i.e., a pressure at which the drilling fluid filter cake is lifted off the filter medium 104 and to flow the screen running fluid through the screen assembly. Valves in fluid communication with first, second, and third lateral ports 114, 116, 118 are closed and second end port 110 is opened and in fluid communication with pump 158. Pump 158 pumps a flowback fluid, for example, base oil, formation fluid, or water, from one of the cylinders through second end port 110. The flowback fluid is pumped at a constant, low rate of, for example 5 ml/min, 10 ml/min, 25 ml/min, 50 ml/min, or any other desired or predetermined rate. The pressures of the fluids above and below the filter medium 104 are measured by pressure gages P1, P2, or differential pressure gage dP1, and monitored over time to determine lift up pressure of the filter cake.

In one embodiment, the flowback fluid flows through second end port 110, up through diverter 132, and through filter medium 104. Diverter 132 diverts the flow of flowback fluid from second end port 110 and disperses or evenly distributes the flow of fluid to the filter medium 104. By distributing the flowback fluid flowing against the filter medium 104, the diverter helps provide a flow of flowback fluid that will allow for more uniform lift off of the filter cake from the filter medium.

The screen running fluid in the test cell above the filter medium 104 is then flowed through the screen assembly 152 and out through first end port 106. Volume of fluid pumped over time and changes in pressure are monitored throughout the flow sequences. In some embodiments, a gravel pack or proppant pack (not shown) is disposed within the test device 100 between the filter medium 104 and the screen assembly 152, by either pumping the proppants in a fluid as for displacement to a screen running fluid or pre-placing the proppant pack in the test device before the test.

Displacing Drilling Fluid to Breaker Fluid for Dynamic Filter Cake

In some embodiments, after the dynamic filter cake has been established, a breaker test with screen assembly may be performed. To displace the drilling fluid from above the filter medium 104 and replace the drilling fluid with a breaker fluid, valves in communication with a first cylinder (e.g., S1) housing the drilling fluid are closed, and valves in communication with a second cylinder (e.g., S2) housing a breaker fluid are opened. The first pump 158 may be used to pump the breaker fluid from the second cylinder to first end port 106 at a desired rate. For example, the first pump 158 may supply breaker fluid at a rate of 10 ml/min, 25 ml/min, 50 ml/min, 100 ml/min, 200 ml/min, 300 ml/min, or any other desired or predetermined rate. As breaker fluid is pumped in through the first end port 106, at least one lateral port above the filter medium 104 is opened to allow for the drilling fluid within the test device 100 to be removed from the test device 100. In one embodiment, valves in fluid communication with first and second lateral port 114, 116 may be alternatingly opened and closed to allow drilling fluid to exit the test device 100 through the first and second lateral ports 114, 116. In some embodiments, the valves in fluid communication with first and second lateral port 114, 116 may be opened simultaneously. In other embodiments, the valves in fluid communication with first and second lateral port 114, 116 may be opened and closed alternatingly and then opened simultaneously. In yet other embodiments, first end port 106 may be closed, breaker fluid may be pumped in through first lateral port 114, and the drilling fluid may be displaced through second lateral port 116. To maintain a temperature of the fluid within the test device 100, the breaker fluid may be heated before entering the test device 100 to a temperature approximately equal to the desired or set temperature of heating cabinet 662, 762. For example, the breaker fluid (or other fluids entering the test device) may be preheated by a heater, coiled tubing for increased friction, etc.

The second pump 160 may provide a constant pressure to the fluid below the filter medium 104. The pressure applied by the first pump 158 to the fluid above the filter medium 104 and the pressure applied by the second pump 160 to the fluid below the filter medium 104 may be approximately equal, such that the pressure differential across the filter medium is approximately zero. For example, the pressure applied by the first and second pumps 158, 160 may be approximately 300 psi, 600 psi, 900 psi, etc.

Once a desired volume of breaker fluid (e.g., a volume of the test device 100 above the filter medium 104 or greater) has been pumped into the test device 100), the valves in fluid communication with first and second lateral port 114, 116 are closed and the first pump 100 is stopped. The second pump 160 is adjusted to maintain a constant pressure below the filter medium 104. For example, second pump 160 may maintain a constant pressure of 50 psi, 100 psi, 200 psi, etc. If desired, the second pump 160 may maintain the constant pressure for a desired amount of time to provide a breaker shut-in, i.e., to allow the breaker fluid to penetrate the dynamic filter cake. For example, the second pump 160 may maintain constant pressure below the filter medium 104 for 15 mins, 30 mins, 45 mins, 1 hour, etc. Fluid may be allowed to bleed out of test device 100 through a relief valve. Subsequently, the constant pressure applied by the second pump 160 may be removed and the pressure decline below the filter medium 104 may be monitored. For example, a valve in fluid connection with the third lateral port 118 may be positioned to redirect flow from between the second pump 160 and the third lateral port 118 to between the third lateral port 118 and a pressure gage P2, which provides a pressure reading for the pressure of the fluid below the filter medium 104. A pressure gage P1 provides a reading for the fluid pressure above the filter medium 104. The rate at which the pressure equalizes across the dynamic filter cake on the filter medium 104 (i.e., rate at which P1 and P2 equalize or dP 1 is zeroed) is monitored.

A flowback sequence may then be performed to determine a lift-up pressure, i.e., a pressure at which the dynamic filter cake is lifted off the filter medium 104 and to flow the breaker fluid through the screen assembly. Valves in fluid communication with first, second, and third lateral ports 114, 116, 118 are closed and second end port 110 is opened and in fluid communication with pump 158. Pump 158 pumps a flowback fluid, for example, base oil, formation fluid, or water, from one of the cylinders through second end port 110. The flowback fluid is pumped at a constant, low rate of, for example 5 ml/min, 10 ml/min, 25 ml/min, 50 ml/min, or any other desired or predetermined rate. The pressures of the fluids above and below the filter medium 104 are measured by pressure gages P1, P2 and monitored over time to determine lift up pressure of the filter cake.

In one embodiment, the flowback fluid flows through second end port 110, up through diverter 132, and through filter medium 104. Diverter 132 diverts the flow of flowback fluid from second end port 110 and disperses or evenly distributes the flow of fluid to the filter medium 104. By distributing the flowback fluid flowing against the filter medium 104, the diverter helps provide a flow of flowback fluid that will allow for more uniform lift off of the dynamic filter cake from the filter medium.

While specific fluid flow sequences are described above, one of ordinary skill in the art will appreciate that various the sequences may be arranged in various orders. For example, in one test, a static filter cake may be established, and a breaker test and a flowback test performed. In another embodiment, a dynamic filter cake may be established and a breaker test and a flowback test performed. In still other embodiment, a dynamic filter cake may be established and a screen running fluid through a screen test and a flowback test performed. In yet another embodiment, a dynamic filter cake may be established, and a breaker test with screen assembly may be performed. In yet other embodiments, a gravel pack may be included with a screen assembly for a statically or dynamically established filter cake and a breaker test and flowback test may be performed. In yet other embodiments, a sealing towards formation with a fluid loss pill through a sand control screen may be performed.

While specific examples are described above with respect to flow from one or more cylinders S1, S2, S3, S4, and by opening, closing, or switching valves along the piping network, one of ordinary skill in the art will appreciate that embodiments of the present disclosure are not limited to such examples. The type, location, and number of valves and cylinders may be varied without departing from the scope of embodiments disclosed herein. Similarly, the configuration of the piping network may be varied without departing from the scope of the present disclosure.

EXAMPLES

Referring back to FIG. 6, a detailed description of one or more procedures that may be used in accordance with the present disclosure is provided. This detailed description of specific processes is meant to provide example procedures that may be used to perform one or more flow sequences with a test device, system, and method of evaluating a well fluid in accordance with embodiments disclosed herein, and is not meant to limit the scope of the disclosure. Reference is made to the various valves, flow lines, cylinders, and pumps shown in the process and instrumentation diagram of FIG. 6. As noted on in the legend in FIG. 6, three way valves used in this example system may be turned to a first position, designated by the letter "V", or a second position, designated by the letter "H". Accordingly, a position of a valve may be indicated as, for example, 8V, wherein valve number 8 is positioned as shown in the legend for "V". Additionally, various fluids may be used in the sequences performed by the system, for example a drilling fluid ("DIF"), a base oil (Base Oil), or a breaker fluid ("Breaker").

Establishing a Filter Cake

To establish a filter cake, the test device 100 is filled with base oil to the top of the filter medium 104 and drilling fluid above the base oil. Alternatively, the test device 100 may be filled with just base oil. The ports at B, C, D, and E are closed on the test cell by a cap. All lines in the piping network are drained with base oil using pump 158. All valves in the piping network, except valves 1-4, 21-24, and 16, are opened. As such, cylinders S1-S4 are initially isolated from the system, and pumps 158, 160 are isolated from one another. The lines are drained through valves 5 and 26 to a drain. Valves 9, 17, 18, and 20 are closed after connecting the lines to the ports at D, E, B, and C, respectively.

Next, the following valves are properly positioned to 8V, 7V, 10H and valve 15 is closed. Valve 16 is positioned to 16H and valves 1 and 2 are opened for pumping drilling fluid from S1 with the second pump 160. Drilling fluid is then bled through valves 8, 7, and 10 to the port at A with the second pump 160. The heating cabinet is then actuated to start heating the test device 100 to 176° F. (80° C.) to allow for heat expansion of the drilling fluid and for air to escape out of the test device, through for example a relief valve in the test device or through the port at A. A section of the piping network is then connected to the port at A. Valves 11-14 are opened to allow for a pressure differential across the filter medium 104 to be measured.

The system is then pressured up to approximately 150 to 200 psi using the second pump 160. The temperature on the heating cabinet is adjusted to increase the temperature of the test device to a required test temperature, for example 212° F. (100° C.) or 356° F. (180° C.). The test device is then allowed to stand for approximately 4 hours. Cylinder S1 is configured to allow for retraction or return of fluid to the cylinder S1 due to heat expansion within the test device 100. After the desired time has lapsed, the pressure is increased to 600 psi or a desired overbalance pressure.

The first pump 158 is pressured up towards closed valves 15 and 16 to 600 psi or the desired overbalance pressure. Valve 16 is then positioned to 16V to allow for fluid communication between the first pump 158 and cylinders S1, S2. The second pump 160 is then set at a constant pressure, for example 100 psi. Valves 22 and 21 are opened, valves 19 and 17 are positioned to 19H and 17H to allow for establishment of the filter cake. The volume pumped versus time and change in pressure for a set time is monitored. The pumping is then stopped.

Displacement to Breaker Fluid

To displace the drilling fluid within the test device, valves 17 and 8 are closed. Pressure is bled off by positioning valve 5V. Valve 5 is then positioned 5H, and valve 2 is closed and then valve 1 is closed. Valve 3 and then valve 4 are opened for pumping breaker fluid from S2. The first pump 158 is pressured up to 600 psi and valve 8 is positioned to 8V. The second pump is then set at a constant pressure of 600 psi. Valve 9 is opened and the first pump is set at a constant rate of 10 ml/min, 25 ml/min, 50 ml/min, 100 ml/min, 200 ml/min, 300 ml/min, or any other desired or predetermined rate.

Valve 20 is positioned to 20H after a predetermined volume is pumped to the test device. Valve 9 is then closed. Valves 9 is then open and closed alternatingly with valve 20H Then, 9 is opened simultaneously with 20H to allow flow of fluid from the test device out through ports at D, C. The first pump is then stopped and valves 9 and 20 are closed. The second pump 160 is set at a constant pressure, for example 100 psi. If applicable, a breaker shut-in time is provided to allow the breaker fluid to break up the established filter cake. Valve 17 is then positioned to 17H and the pressure decline across the filter medium is monitored.

Flowback

After the drilling fluid has been displaced by the breaker fluid, a flow back test or pressure decline used for breakthrough may be performed. Valve 17 is closed, then valves 4 and 3 are closed. Valve 16 is closed and valve 15 is opened. Valve 8 is positioned 8H, valve 21 is closed, and valve 26 is positioned to 26H to allow for draining the line of breaker fluid. Base oil is then slowly drained through to valve 26 by pump 158. Valve 26 is positioned to 26V and valve 21 is opened. Valves 7 and 19 are positioned to 7H and 19V. Valve 18 is opened and pump 158 pumps a fluid, for example base oil, formation fluid, or water, at a constant rate through the port at B, up through diverter 132. Pressure within the test device 100 versus time is monitored.

Establishing a Dynamic Filter Cake

To establish a filter cake, the test device 100 is filled with base oil to the top of the filter medium 104 and drilling fluid above the base oil. Alternatively, the test device 100 may be filled with just base oil. The ports at B, C, D, and E are closed on the test cell by a cap. All lines in the piping network are drained with base oil using pump 158. All valves in the piping network, except valves 1-4, 21-24, and 16, are opened. As such, cylinders S1-S4 are initially isolated from the system, and pumps 158, 160 are isolated from one another. The lines are drained through valves 5 and 26 to a drain. Valves 9, 17, 18, and 20 are closed after connecting the lines to the ports at D, E, B, and C, respectively.

Next, valve 15 is closed, and valve 16 is positioned to 16H. Valves 1 and 2 are opened for pumping drilling fluid from S1 with the second pump 160. Valve 8 is positioned to 8H and valve 9 is opened. Drilling fluid is then bled through valves 8 and 9 to the port at D with the second pump 160. A section of the piping network is then connected to the port at D. The heating cabinet is then actuated to start heating the test device 100 to 176° F. (80° C.) to allow for heat expansion of the drilling fluid and for air to escape out of the test device, through for example a relief valve in the test device or through the port at A. The following valves are then positioned to 8V, 7V, and 10H. A section of the piping network is then connected to the port at A. Valves 11-14 are opened to allow for a pressure differential across the filter medium 104 to be measured.

The system is then pressured up to approximately 150 to 200 psi using the second pump 160. The temperature on the heating cabinet is adjusted to increase the temperature of the test device to a required test temperature, for example 212° F. (100° C.) or 356° F. (180° C.). The test device is then allowed to stand for approximately 4 hours. Cylinder S1 is configured to allow for retraction or return of fluid to the cylinder S1 due to heat expansion within the test device 100. After the desired time has lapsed, the pressure is increased to 600 psi or a desired overbalance pressure. Valve 10 is positioned to 10V to get 600 psi to valve 20. Valve 7H is positioned and 19V is positioned.

The first pump 158 is pressured up towards closed valves 15 and 16 to 600 psi or the desired overbalance pressure. Valve 16 is then positioned to 16V to allow for fluid communication between the first pump 158 and cylinders S1, S2. Valves 22 and 21 are opened, and valve 8 is positioned to 8H. Pressure provided by the first pump 158 may be re-established at 600 psi. Valve 9 is opened and valve 20 is positioned to 20V. The first pump 158 is set at a constant rate of 10 ml/min, 25 ml/min, 50 ml/min, 100 ml/min, 200 ml/min, 300 ml/min, or any other desired or predetermined rate and valve 17 is positioned 17V to allow for establishment of the filter cake. The volume pumped versus time and change in pressure for a set time is monitored. The pumping is then stopped.

Advantageously, embodiments disclosed herein provide for a well fluid test device and method of evaluating a well fluid that allow for establishment of a filter cake within a test device and multiple flow sequences without loss of temperature, pressure, or damage to the filter cake. A test device in accordance with embodiments disclosed herein allows for static and/or dynamic filter cakes to be established and multiple sequences to be performed without having to disassemble the test device between fluid flow sequences. The temperature and pressure within the test device may be maintained or controlled throughout multiple flows sequences. Advantageously, a well fluid test device and method of evaluating a well fluid in accordance with the present disclosure provide multiple fluid sequences without the need to disassemble the test device, release the temperature, or release the pressure within the test device.

Advantageously, a test device and method in accordance with embodiments disclosed herein may allow multiple fluids to be displaced without the release of temperature and pressure on the system over a filter medium. Maintaining temperature and pressure across the filter medium may allow for a filter cake to be established statically or dynamically, spacer fluids to be displaced across the filter cake, and filter cake or filter cake residuals to be flowed back after a breaker fluid is injected over the filter cake. To ensure the flow of fluids across an established filter cake surface, adjustable spacer rings may be placed below or above the filter medium. The spacer rings may be of varying heights to accommodate varying filter cake thicknesses.

A test device in accordance with the present disclosure includes one or more side ports. A side port underneath the filter medium may be used to measure filtrate fluid loss through the filter medium, which may leave the second end port to be used solely as a flowback line inlet. Using the second end port for only flowback and having a third lateral port below the filter medium may reduce the risk of blocking the flowback outlet and mis-readings of filter cake formation. A test device in accordance with embodiments disclosed herein also provides a diverter that may optimize flowback fluid for a more uniform flowback/liftoff of the filter cake, rather than just centered penetration through the filter medium.

Embodiments disclosed herein also advantageously provide a test device that includes a screen assembly for sand control evaluation. With the screen assembly placed above a dynamically established filter cake, flowback of drilling fluid filter cake and screen running fluids through a sand control screen assembly may be evaluated. Additionally, a gravel pack may be placed between the screen assembly and the filter medium and a flowback of filter cake or filter cake residuals performed.

A test device as described herein may advantageously be mounted in a holder that allows for the test device to be arranged at any angle from vertical to horizontal. All fluid processes and sequences may be monitored through pressure gages (differential and/or absolute) across the filter medium, temperature gages, and pressure gages and flow meters at the pumps or along the piping network.

Although only a few example embodiments have been described in detail above, those skilled in the art will readily appreciate that many modifications are possible in the example embodiments without materially departing from the scope of the present disclosure. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

What is claimed:

1. A well fluid test device comprising:
   a cell body comprising:
      a first end port disposed on an upper end of the cell body;
      a second end port disposed on a lower end of the cell body;
      a first lateral port disposed on a side of the cell body; and
      a second lateral port disposed on a side of the cell body;
   a filter medium disposed in the cell body, wherein the first and second lateral ports are disposed above the filter medium; and
   a filter medium holder ring and a filter medium support disposed in the cell body and configured to receive the filter medium.

2. The well fluid test device of claim 1, further comprising a first end cap disposed on the upper end of the cell body and a second end cap disposed on the lower end of the cell body.

3. The well fluid test device of claim 1, further comprising at least one of a spacer ring disposed above or below the filter medium and a flow diverter disposed in the cell body below the filter medium.

4. The well fluid test device of claim 1, further comprising a third lateral port disposed on a side of the cell body below the filter medium.

5. The well fluid test device of claim 1, further comprising:
- an inner body disposed in the cell body above the filter medium; and
- a screen assembly, the screen assembly comprising:
  - a screen holder disposed in the inner body; and
  - a screen disposed in the screen holder.

6. A method of evaluating a well fluid comprising:
- injecting a first fluid into a well fluid test device, the well fluid test device having (a cell body and) a filter medium (disposed in the cell body and dividing the cell body into an upper chamber and a lower chamber, the cell body further including at least three ports above the filter medium and at least one port below the filter medium);
- heating the fluid in the well fluid test device;
- establishing a pressure differential across the filter medium;
- establishing a filter cake on the filter medium; and
- injecting a second fluid into the well fluid test device while maintaining at least one of a temperature and a pressure in the well fluid test device; and
- displacing the first fluid in the well fluid test device with the second fluid.

7. The method of claim 6, wherein the at least three ports above the filter medium comprise a first end port and the at least one port below the filter medium comprises a lateral port, and wherein the establishing a pressure differential across the filter medium comprises:
- pressurizing the well fluid test device through the first end port of the well fluid test device; and
- pressurizing the well fluid test device through the lateral port of the well fluid test device disposed below the filter medium.

8. The method of claim 7, wherein the pressurizing the well fluid test device through the first end port of the well fluid test device comprising pumping, with a first pump, fluid through the first end port; and wherein the pressurizing the well fluid test device through the lateral port of the well fluid test device disposed below the filter medium comprises pumping, with a second pump, fluid through the lateral port.

9. The method of claim 6, further comprising injecting a drilling fluid above the first fluid, wherein the first fluid is a base oil.

10. The method of claim 6, wherein the second fluid is a breaker fluid, displacing comprising:
- bleeding off a predetermined pressure from the well fluid test device;
- pumping a volume of breaker fluid in through a first port of the at least three ports above the filter medium; and
- displacing the first fluid in the well fluid test device out of a second port of the at least three ports above the filter medium.

11. The method of claim 10, wherein the first port is one of a first end port and a first lateral port disposed above the filter medium, and wherein the second port a second lateral port disposed above the filter medium.

12. The method of claim 10, further comprising shutting in the well fluid test device.

13. The method of claim 10, further comprising:
- opening the at least one port of the well fluid test device below the filter medium; and
- monitoring a rate of pressure equalization across the filter medium.

14. The method of claim 6, further comprising pumping a flowback fluid, through the at least one of a port disposed below the filter medium or a diverter disposed in the well fluid test device below the filter medium.

15. The method of claim 14, further comprising monitoring pressure across the filter medium.

16. The method of claim 6, wherein the at least three ports above the filter medium includes a first lateral port and a second lateral port, wherein the at least one port below the filter medium includes a third lateral port, and wherein the establishing a pressure differential across the filter medium comprises:
- pumping the second fluid into the well fluid test cell through the first lateral port of the well fluid test device disposed above the filter medium;
- opening the second lateral port of the well fluid test device disposed above the filter medium; and
- opening the third lateral port of the well fluid test device disposed below the filter medium.

17. The method of claim 6, wherein the at least three ports above the filter medium comprises a first end port and a lateral port, and wherein the method further comprises displacing the first fluid above the filter medium of the well fluid test device after establishing the filter cake, the displacing comprising:
- pumping a screen running fluid into the well fluid test device through the first end port; and
- opening the lateral port of the well fluid test device disposed above the filter medium.

18. The method of claim 17, further comprising:
- pumping a flowback fluid through the at least one port below the filter medium; and
- pumping the flowback fluid and screen running fluid through a screen disposed above the filter medium.

19. A method of evaluating a well fluid comprising:
- assembling a well fluid test device having a cell body and a filter medium disposed therein and dividing the cell body into an upper chamber and a lower chamber, the cell body further including at least three ports above the filter medium and at least one port below the filter medium;
- establishing a filter cake in on the filter medium; and
- performing at least one test sequence in the well fluid test device after establishing the filter cake and controlling at least one of a temperature and pressure of the test device while performing the at least one test sequence, wherein the at least one test sequence is one selected from a group consisting of a displacement of a well fluid from the test device and replacing the fluid with a second well fluid, a flowback with a fluid through the filter medium and the filter cake, flowing a fluid back through a screen assembly, and flowing a fluid back through a gravel pack.

* * * * *